United States Patent
Karau et al.

(10) Patent No.: US 6,813,333 B2
(45) Date of Patent: Nov. 2, 2004

(54) METHODS AND APPARATUS FOR DETECTING STRUCTURAL, PERFUSION, AND FUNCTIONAL ABNORMALITIES

(75) Inventors: Kelly Lynn Karau, New Berlin, WI (US); John Michael Sabol, Sussex, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 106 days.

(21) Appl. No.: 10/306,467

(22) Filed: Nov. 27, 2002

(65) Prior Publication Data

US 2004/0101089 A1 May 27, 2004

(51) Int. Cl.[7] .............................................. G01N 23/00
(52) U.S. Cl. .................................... 378/4; 378/5; 378/19
(58) Field of Search ......................... 378/4, 19, 5, 98.9, 378/8, 901

(56) References Cited

U.S. PATENT DOCUMENTS

| | | | | |
|---|---|---|---|---|
| 4,361,901 A | | 11/1982 | Daniels et al. | |
| 4,445,226 A | * | 4/1984 | Brody | 378/98.9 |
| 4,890,310 A | * | 12/1989 | Umetani et al. | 378/82 |
| 5,485,492 A | * | 1/1996 | Pelc | 378/5 |
| 5,533,080 A | * | 7/1996 | Pelc | 378/5 |
| 5,570,403 A | | 10/1996 | Yamazaki et al. | |
| 5,665,971 A | | 9/1997 | Chen et al. | |
| 6,018,562 A | | 1/2000 | Willson | |
| 6,185,272 B1 | | 2/2001 | Hiraoglu et al. | |
| 6,236,709 B1 | | 5/2001 | Perry et al. | |
| 6,320,931 B1 | | 11/2001 | Arnold | |
| 6,369,389 B1 | | 4/2002 | Berlad et al. | |
| 6,507,633 B1 | | 1/2003 | Elbakri et al. | |
| 6,560,315 B1 | | 5/2003 | Price et al. | |
| 2002/0163988 A1 | | 11/2002 | Nisius et al. | |
| 2003/0063787 A1 | | 4/2003 | Natanzon et al. | |

* cited by examiner

Primary Examiner—Craig E. Church
Assistant Examiner—Irakli Kiknadze
(74) Attorney, Agent, or Firm—Carl B. Horton, Esq.; Armstrong Teasdale LLP

(57) ABSTRACT

A method for obtaining data includes scanning a lung of a patient with a Multi-Energy Computed Tomography (MECT) system to acquire data regarding a plurality of contrast agents.

26 Claims, 4 Drawing Sheets

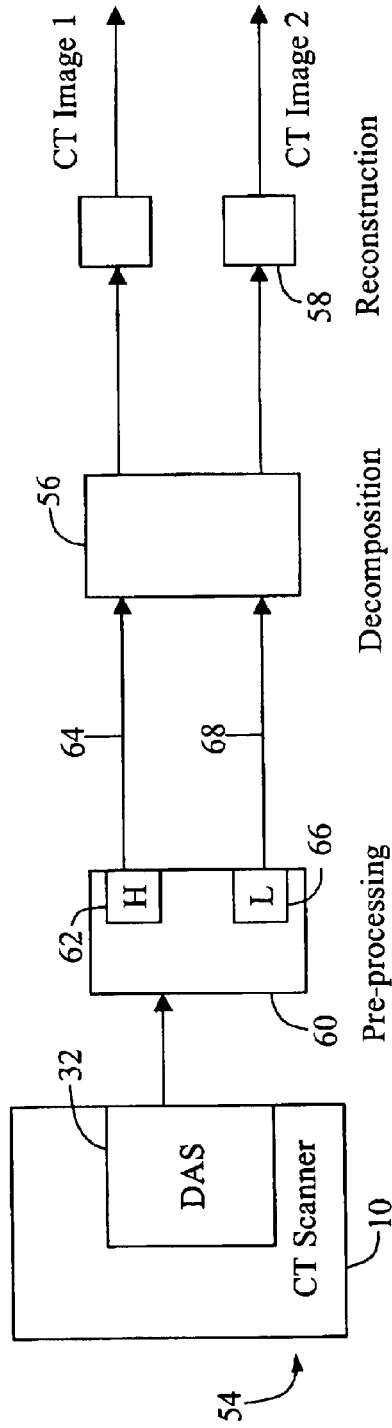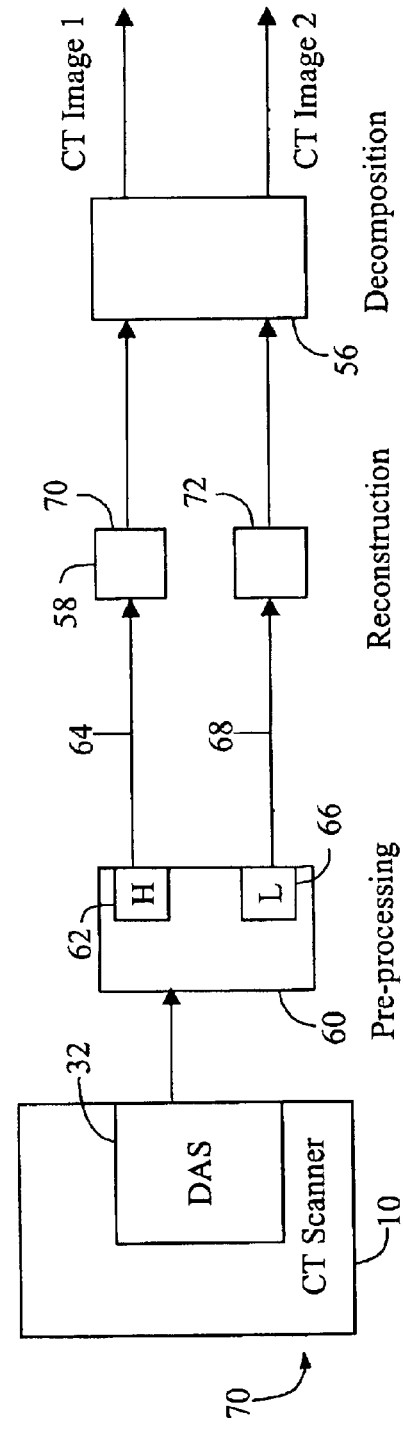

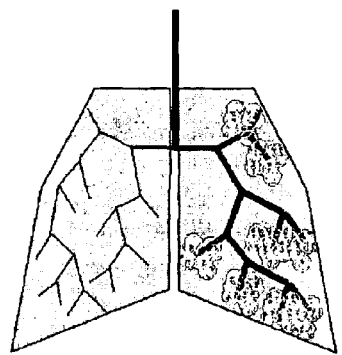
FIG. 5
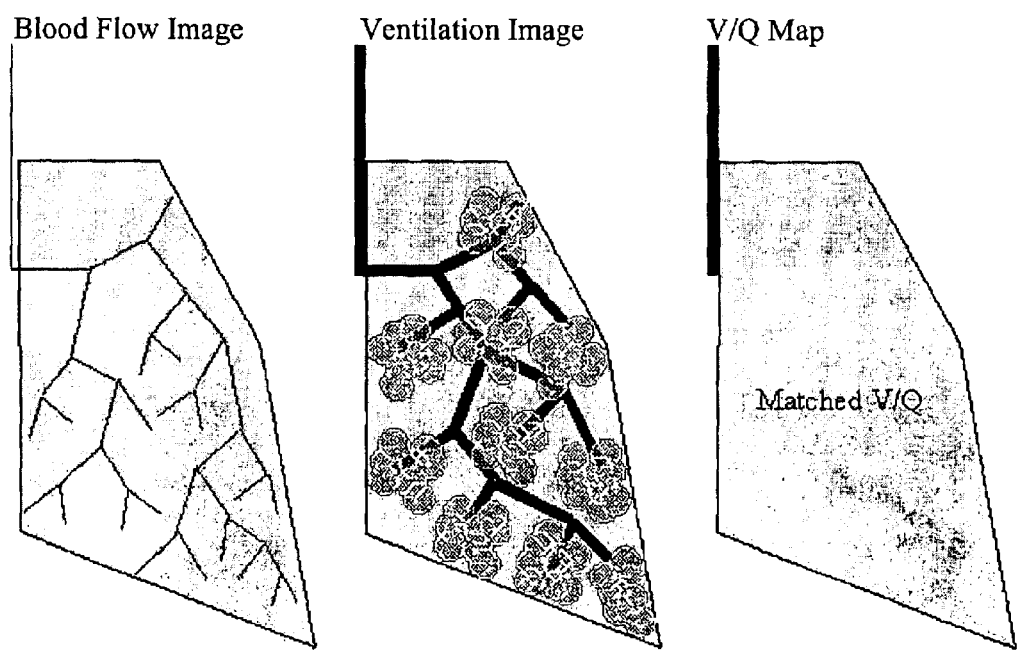
FIG. 6 Matched V/Q

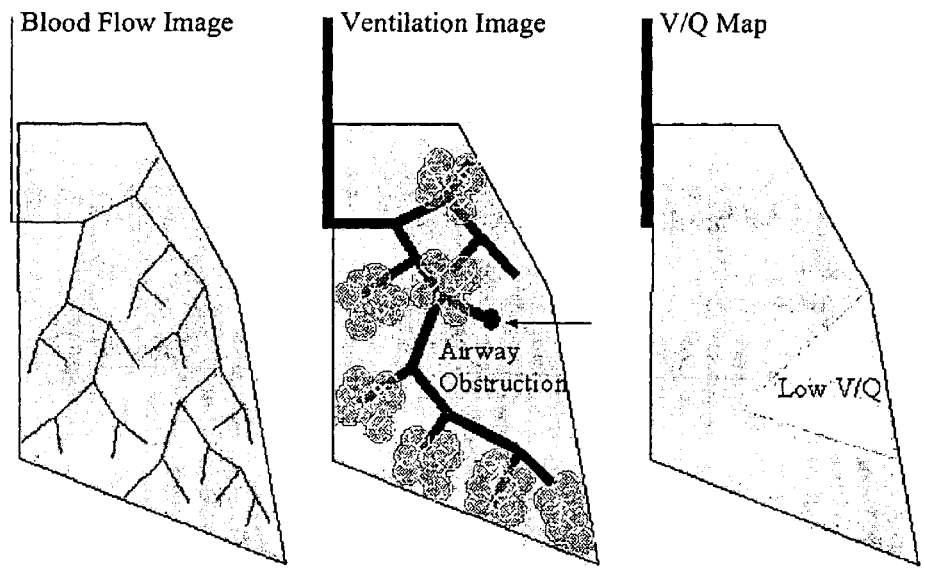
FIG. 7 Airway Obstruction
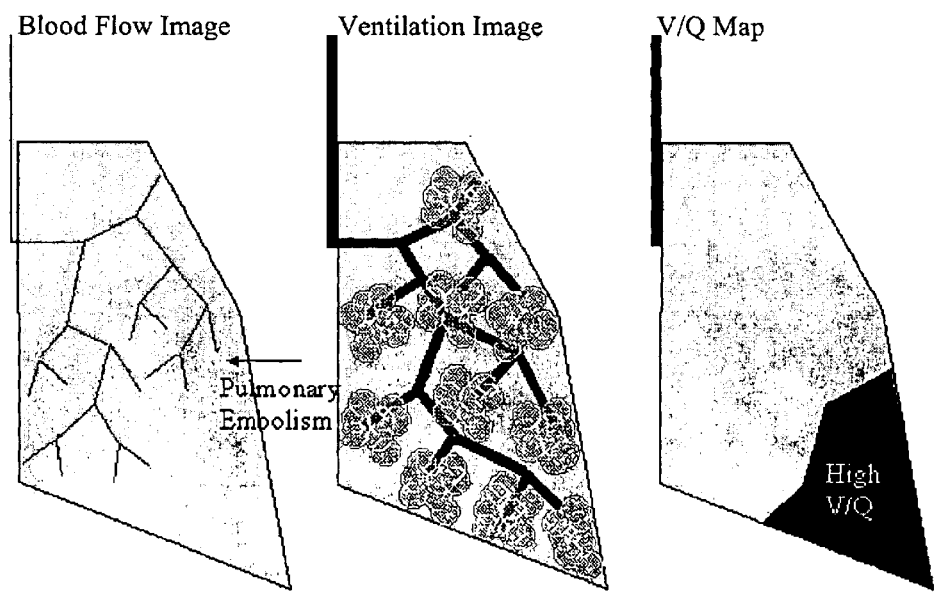
FIG. 8 Pulmonary Embolism

US 6,813,333 B2

METHODS AND APPARATUS FOR DETECTING STRUCTURAL, PERFUSION, AND FUNCTIONAL ABNORMALITIES

BACKGROUND OF THE INVENTION

This invention relates to computed tomographic (CT) imaging, and more particularly to methods and apparatus for the detection and diagnosis of lung abnormalities.

In spite of recent advancements in computed tomography (CT) technology, such as faster scanning speeds, larger coverage with multiple detector rows, and thinner slices, energy resolution is still a missing piece. Namely, wide x-ray photon energy spectrum from the x-ray source and the lack of energy resolution from CT detection systems preclude energy discrimination CT.

X-ray attenuation through a given object is not a constant. Rather, the X-ray attenuation is strongly dependent on the x-ray photon energy. This physical phenomenon manifests itself in the image as beam-hardening artifacts, such as, nonuniformity, shading, and streaks. Some beam-hardening artifacts can be easily corrected, but other beam-hardening artifacts may be more difficult to correct. In general, known methods to correct beam hardening artifacts include water calibration, which includes calibrating each CT machine to remove beam hardening from materials similar to water, and iterative bone correction, wherein bones are separated in the first-pass image then correcting for beam hardening from the bones in the second-pass. However, beam hardening from materials other than water and bone, such as metals and contrast agents, may be difficult to correct. In addition, even with the above described correction methods, conventional CT does not provide quantitative image values. Rather, the same material at different locations often shows different CT numbers.

Another drawback of conventional CT is a lack of material characterization. For example, a highly attenuating material with a low density can result in the same CT number in the image as a less attenuating material with a high density. Thus, there is little or no information about the material composition of a scanned object is based solely on the CT number. At least some state-of-the-art CT scanners currently available are limited to providing anatomical information. For lung scans, images produced by such scanners exhibit a significant level of image artifacts and CT number inaccuracy. These limitations prevent the utilization of the CT device for advanced diagnosis. Accordingly, the methods and apparatus described herein address the detection and diagnosis of lung abnormalities.

BRIEF DESCRIPTION OF THE INVENTION

In one aspect, a method for obtaining data is provided. The method includes scanning a lung of a patient with a Multi-Energy Computed Tomography (MECT) system to acquire data regarding a plurality of contrast agents In another aspect, a Multi-Energy Computed Tomography (MECT) System is provided. The MECT includes a radiation source, a radiation detector, and a computer operationally coupled to the radiation source and the radiation detector. The computer is configured to receive data regarding a first energy spectrum of a scan of a lung of a patient, receive data regarding a second energy spectrum of the scan of the lung, generating a first functional image using data regarding a first contrast agent, and generating a second functional image using data regarding a second contrast agent.

In yet another aspect, a Multi-Energy Computed Tomography (MECT) System is provided. The MECT includes a radiation source, a radiation detector, and a computer operationally coupled to the radiation source and the radiation detector. The computer is configured to receive data regarding a first energy spectrum of a scan of a lung of a patient, receive data regarding a second energy spectrum of the scan, and decompose the received data to generate data regarding a plurality of contrast agents.

In still another aspect, a computer readable medium is encoded with a program. The program is configured to instruct a computer to receive data regarding a first energy spectrum of a scan of a lung of a patient, receive data regarding a second energy spectrum of the scan, and decompose the received data to generate data regarding a plurality of contrast agents.

In yet still another aspect, a computer readable medium is encoded with a program. The program is configured to instruct a computer to scan a lung of a patient with a Multi-Energy Computed Tomography (MECT) system to acquire data regarding a first contrast agent in a gaseous medium and a second contrast agent in a liquid medium, generate a first functional image using data regarding the first contrast agent, and generate a second functional image using data regarding the second contrast agent.

In another aspect a method for obtaining data is provided. The method includes administering a gaseous contrast agent to a patient, administering a liquid contrast agent to the patient, and imaging the patient to obtain data regarding the gaseous contrast agent and the liquid contrast agent.

BRIEF DESCRIPTION OF THE DRAWINGS

FIG. 3 is a flow chart representing a pre-reconstruction analysis.

FIG. 4 is a flow chart representing a post-reconstruction analysis.

FIG. 5 is a schematic view of Lung Ventilation and Perfusion systems.

FIG. 6 illustrates examples of ventilation perfusion maps.

FIG. 7 illustrates an example where a V/Q map has light gray areas that indicate ventilation is less than perfusion.

FIG. 8 illustrates an example where areas of very dark color indicate that perfusion is less than ventilation.

DETAILED DESCRIPTION OF THE INVENTION

Figure 1:
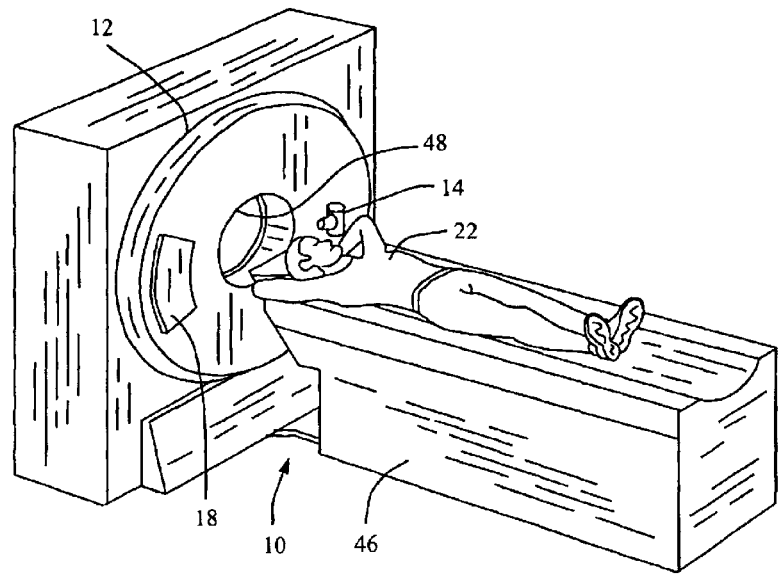
FIG. 1 is a pictorial view of a MECT imaging system.

The methods and apparatus described herein address the detection and diagnosis of abnormalities in the lung regions of a patient by employing novel approaches that make use of basic properties of the x-ray and material interaction. For each ray trajectory, multiple measurements regarding different mean x-ray energies are acquired. As explained in greater detail below, when Basis Material Decomposition (BMD) and Compton and photoelectric decomposition are performed on these measurements, additional information is obtained that enables improved accuracy and characterization.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Herein are described methods and apparatus for detecting structural, perfusion, and functional abnormalities in lung tissue using an energy-discriminating (also known as multi-energy) computed tomography (MECT) system. First described is MECT system 10 and followed by lung applications using MECT system 10.

Energy Discrimination (Multi-Energy) CT System 10

Figure 2:
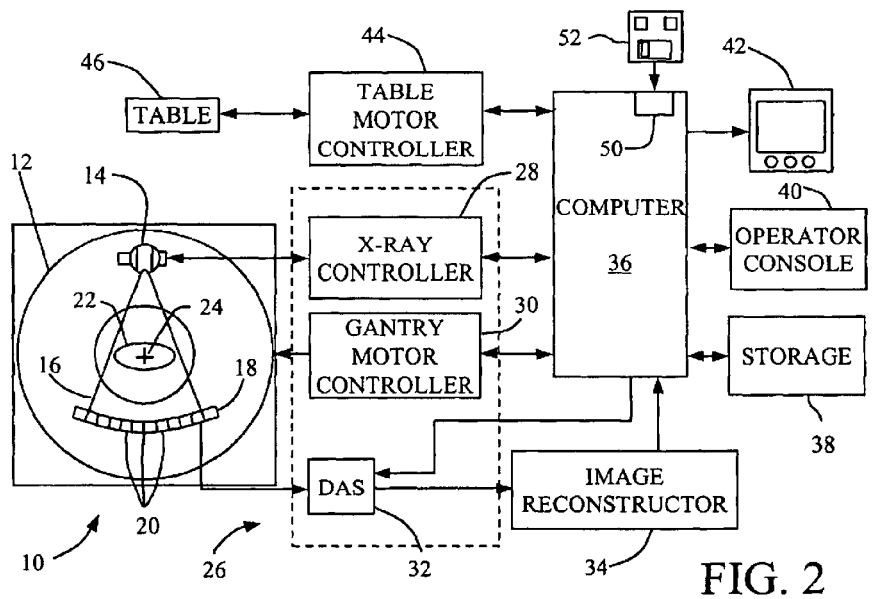
FIG. 2 is a block schematic diagram of the system illustrated in FIG. 1.

Referring to FIGS. 1 and 2, a multi-energy scanning imaging system, for example, a multi-energy multi-slice computed tomography (MECT) imaging system 10, is shown as including a gantry 12 representative of a "third generation" CT imaging system. As used herein, a multi-energy computed tomography system may also be referred to as an energy discrimination CT (EDCT) system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of MECT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD, a MOD or an other digital source such as a network or the Internet, as well as yet to be developed digital means. Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT imaging system 10 is an energy-discriminating (also known as multi-energy) computed tomography (MECT) system in that system 10 is configured to be responsive to different x-ray spectra. This can be accomplished with a conventional third generation CT system to acquire projections sequentially at different x-ray tube potentials. For example, two scans are acquired either back to back or interleaved in which the tube operates at 80 kVp and 160 kVp potentials, for example. Alternatively, special filters are placed between the x-ray source and the detector such that different detector rows collect projections of different x-ray energy spectrum. Alternatively, the special filters that shape the x-ray spectrum can be used for two scans that are acquired either back to back or interleaved. Yet another embodiment is to use energy sensitive detectors such that each x-ray photon reaching the detector is recorded with its photon energy. Although the specific embodiment mentioned above refers to a third generation CT system, the methods described herein equally apply to fourth generation CT systems (stationary detector—rotating x-ray source) and fifth generation CT systems (stationary detector and x-ray source).

There are different methods to obtain multi-energy measurements: (1) scan with two distinctive energy spectra, (2) detect photon energy according to energy deposition in the detector, and (3) photon counting. Photon counting provides clean spectra separation and an adjustable energy separation point for balancing photon statistics.

MECT facilitates reducing or eliminating a plurality of problems associated with conventional CT, such as, but not limited to, a lack of energy discrimination and material characterization. In the absence of object scatter, one only need system 10 to separately detect two regions of photon energy spectrum: the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation: (1) Compton scatter and the (2) photoelectric effect. Thus, detected signals from two energy regions provide sufficient information to resolve the energy dependence of the material being imaged. Furthermore, detected signals from two energy regions provide sufficient information to determine the relative composition of an object composed of two materials.

In an exemplary embodiment, MECT uses a decomposition algorithm, such as, but not limited to, a CT number difference algorithm, a Compton and photoelectric decomposition algorithm, a basis material decomposition (BMD) algorithm, and a logarithm subtraction decomposition (LSD) algorithm.

The CT number difference algorithm includes calculating a difference value in a CT or a Hounsfield number between two images obtained at different tube potentials. In one embodiment, the difference values are calculated on a pixel-by-pixel basis. In another embodiment, average CT number differences are calculated over a region of interest. The Compton and photoelectric decomposition algorithm includes acquiring a pair of images using MECT 10, and separately representing the attenuations from Compton and photoelectric processes. The BMD algorithm includes acquiring two CT images, wherein each image represents the equivalent density of one of the basis materials. Since a material density is independent of x-ray photon energy, these images are approximately free of beam-hardening artifacts. Additionally, an operator can choose the basis material to target a certain material of interest, thus enhancing the image contrast. In use, the BMD algorithm is based on the concept that the x-ray attenuation (in the energy region for medical CT) of any given material, can be represented by proper density mix of other two given materials, accordingly, these two materials are called the basis materials. In one embodiment, using the LSD algorithm, the images are acquired with quasi-monoenergetic x-ray spectra, and the imaged object can be characterized by an effective attenuation coefficient for each of the two materials, therefore the LSD algorithm does not incorporate beam-hardening corrections. Additionally, the LSD algorithm is not calibrated, but uses a determination of the tissue cancellation parameters, which are the ratio of the effective attenuation coefficient of a given material at the average energy of each exposure. In an exemplary embodiment, the tissue cancellation parameter is primarily dependent upon the spectra used to acquire the images, and on any additional factors that change the measured signal intensity from that which would be expected for a pair of ideal, mono-energetic exposures.

It should be noted that in order to optimize a multi-energy CT system, the larger the spectra separation, the better the image quality. Also, the photon statistics in these two energy regions should be similar, otherwise, the poorer statistical region will dominate the image noise.

Lung Applications of Energy Discriminating using Multi-Energy CT System 10

The present invention applies the above principle to lung studies. In specific, MECT system 10 is utilized to produce CT images as herein described. A pre-reconstruction analysis, a post-reconstruction analysis, and a scout image analysis are three techniques that can be used with MECT system 10 for tissue characterization.

FIG. 3 is a flow chart representing a pre-reconstruction analysis 54 wherein a decomposition 56 is accomplished prior to a reconstruction 58. Computer 36 collects the acquired projection data generated by detector array 18 (shown in FIG. 1) at discrete angular positions of the rotating gantry 12 (shown in FIG. 1), and passes the signals to a preprocessor 60. Preprocessor 60 re-sorts the projection data received from computer 36 to optimize the sequence for the subsequent mathematical processing. Preprocessor 60 also corrects the projection data from computer 36 for detector temperature, intensity of the primary beam, gain and offset, and other deterministic error factors. Preprocessor 60 then extracts data corresponding to a high-energy view 62 and routes it to a high energy channel path 64, and routes the data corresponding to a low-energy views 66 to a low energy path 68. Using the high energy data and low energy data, a decomposition algorithm is used to produce two streams of projection data, which are then reconstructed to obtain two individual images pertaining to two different materials.

FIG. 4 is a flow chart representing a post-reconstruction analysis wherein decomposition 56 is accomplished after reconstruction 58. Computer 36 collects the acquired projection data generated by detector array 18 (shown in FIG. 1) at discrete angular positions of rotating gantry 12 (shown in FIG. 1), and routes the data corresponding to high-energy views 62 to high energy path 64 and routes the data corresponding to low-energy views 66 to low energy path 68. A first CT image 70 corresponding to the high-energy series of projections 62 and a second CT image 72 corresponding to low-energy series of projections 66 are reconstructed 58. Dual-energy decomposition 56 is then performed using a decomposition algorithm to obtain two individual images respectively, pertaining to two different materials. In scout image analysis, the signal flow can be similar to FIG. 3 or FIG. 4. However, the table is moved relative to the gantry to acquire the data.

One common cause of a ventilation perfusion mismatch is pulmonary embolization. However, any cause of pulmonary artery obstruction (bronchogenic carcinoma, lymphoma, metastatic disease, sarcoma, aneurysm, sarcoid, and fungal or granulomatous infection) can produce the same findings. In some known clinical practices, ventilation-perfusion scans are acquired with limited spatial resolution using positron emission tomography (PET) requiring the injection of radioactive isotopes. Similarly, dual scans are required which present difficulty in registering anatomy between the two scans, especially in the case where the scan times or scan interval is long enough to create motion-related artefacts. Multiple energy computed tomography (MECT) ventilation-perfusion maps are generated by simultaneously injecting IV contrast, such as an ionic or non-ionic iodine-based (I) agent such as Iopamidol, chelates of gadolinium such as Gd-DTPA, or non-ionic chelates such as gadodiamide (gadolinium-diethylenetriamine pentaacetic acid bismethylamide, $C_{16}H_{28}GdN_5O_9xH_2O$), to a patient while he/she inhales a stable non-radioactive gas usually having a high atomic number and or density such as $Xe^{131}$. A single scan is acquired and the ratio of Hounsfield units in CT pixel data reconstructed at each of multiple energies provides a 3-dimensional ventilation-perfusion map. The resulting image has significant clinical value. Two major applications are detection of pulmonary emboli and assessment of regional lung function. When a blood clot blocks a pulmonary artery, blood flow ceases to the lung region normally supplied by that vessel, and a corresponding "perfusion defect" results. Such a defect manifest itself as a "high" signal in a ventilation/perfusion map as described below (V/Q map) indicating an area where oxygen exchange is inefficient.

In use, and in accordance with one embodiment, a patient breathes one full breath of $Xe^{131}$ and a substantially simultaneous (timed) Bolus injection of a contrast medium (I) is done. Multiple Energy CT scan data is collected with system 10 at Total Lung Capacity (TLC). The collected data is decomposed using one of the decomposition methods described above (CT Number Difference, Compton and Photoelectric Decomposition, Basis Material Decomposition, or Logarithm Subtraction Decomposition), MECT images are acquired with x-ray spectra or energy discrimination to highlight the differences between the relevant atoms of the administered contrast agents (eg: $Xe^{131}$ and I) The decomposition step yields two image data sets, one (the ventilation functional image, "V" image) emphasizing the density of $Xe^{131}$; the other (the perfusion functional image, "Q" image) illustrating the density of I.

After the two functional images are generated, a V/Q signal from the images is calculated. In one embodiment, the two functional images are registered with each other and a V/Q signal is calculated on a pixel-by-pixel basis, wherein the ratio of CT numbers in the V image to the CT numbers of the Q image represents the V/Q signal for each location in the two images. The V/Q map can be presented by displaying the 3-dimensional lung anatomy via a traditional grayscale image with the V/Q ratios superimposed using a colormap. The traditional grayscale image is an anatomical image and not a functional image. This provides an anatomical map of oxygen exchange efficiency. Using any combination of the acquired images, V, Q, and/or V/Q map data, an observer or computer algorithm can highlight regions of suspicious V/Q. A computer aided detection or diagnosis algorithm can use the data to determine diagnosis of pathologies such as Chronic Obstructive Pulmonary Disease (COPD) and emphysema, or detect, quantify, and classify pathological regions of poor pulmonary function.

FIG. 5 is a schematic view of Lung Ventilation and Perfusion systems showing an Arterial/Venous network on the left side of FIG. 5 and an Airway/Bronchial network on the right side of FIG. 5. Abnormalities in either of these networks will result in V/Q mismatch, ratios inconsistent with the overall V/Q activity of the entire pulmonary anatomy.

FIG. 6 illustrates examples of ventilation perfusion maps including a Perfusion Image showing a vascular network on the left side, a Ventilation Image with bronchial and alveolar network illustrated in the middle, and a ratio of Middle to Left image (V/Q Map) on the right side of FIG. 6. A medium gray area indicates ventilation and perfusion are matched. FIG. 7 illustrates an example where the V/Q map has light gray areas that indicate ventilation is less than perfusion and potential respiratory obstruction may exist. Similarly, FIG. 8 illustrates an example where areas of very dark color indicate that perfusion is less than ventilation and a potential for arterial blockage or pulmonary embolism may exist.

The herein described methods and apparatus facilitate characterizing lung tissue which facilitates the diagnosis of abnormalities in an efficient and cost effective manner.

While the invention has been described in terms of various specific embodiments, those skilled in the art will recognize that the invention can be practiced with modification within the spirit and scope of the claims.

What is claimed is:

1. A method for obtaining data, said method comprising scanning a lung of a patient with a Multi-Energy Computed Tomography (MECT) system to substantially simultaneously acquire data regarding a plurality of contrast agents.

2. A method in accordance with claim 1 further comprising:
generating a first functional image using data regarding a first contrast agent; and
generating a second functional image using data regarding a second contrast agent.

3. A method in accordance with claim 1 further comprising:
administering a first contrast agent in a gaseous state to the patient; and
administering a second contrast agent in a liquid state to the patient.

4. A method in accordance with claim 3 wherein said administering a first contrast agent comprises administering a first contrast agent comprising Xenon.

5. A method in accordance with claim 4 wherein said administering a second contrast agent comprises administering a second contrast agent comprising Iodine or Gadolinium.

6. A method in accordance with claim 1 further wherein said scanning comprises scanning the patient at Total Lung Capacity (TLC).

7. A method in accordance with claim 1 wherein to generate the first and second images, said method further comprises decomposing the acquired data.

8. A method in accordance with claim 7 further comprising performing a Basis Material Decomposition (BMD) of the acquired data.

9. A method in accordance with claim 7 further comprising performing a Computed Tomography (CT) Difference Decomposition of the acquired data.

10. A method in accordance with claim 7 further comprising performing a Compton and Photoelectric Decomposition of the acquired data.

11. A method in accordance with claim 7 further comprising performing a Logarithm Subtraction Decomposition of the acquired data.

12. A method for obtaining data, said data method comprising: scanning a lung of a patient with a Multi-Energy Computer Tomography (MECT) system to acquire data regarding a plurality of contrast agents; generating a first functional image using data regarding a first contrast agent; generating a second functional image using data regarding a second contrast agent; and registering the first functional image with the second functional image.

13. A method in accordance with claim 12 further comprising generating a ratio map on a pixel by pixel basis between the registered first and second images.

14. A method in accordance with claim 13 further comprising displaying the ratio map in color as an overlay to a grayscale anatomical image of the lung.

15. A Multi-Energy Computed Tomography (MECT) System comprising:
   a radiation source;
   a radiation detector; and
   a computer operationally coupled to said radiation source and said radiation detector, said computer configured to:
   receive data regarding a first energy spectrum of a scan of a lung of a patient;
   receive data regarding a second energy spectrum of the scan of said lung;
   generating a first functional image using data regarding a first contrast agent; and
   generating a second functional image using data regarding a second contrast agent.

16. A MECT system in accordance with claim 15 wherein said computer further configured to perform a Compton and photoelectric decomposition of the received data.

17. A MECT system in accordance with claim 15 wherein said computer further configured to perform a Basis Material Decomposition (BMD) of the received data.

18. A MECT system in accordance with claim 15 wherein said computer further configured to perform a Computed Tomography (CT) Difference Decomposition of the received data.

19. A MECT system in accordance with claim 15 wherein said computer further configured to perform a Logarithm Subtraction Decomposition of the received data.

20. A MECT system in accordance with claim 15 wherein said computer further configured to generate a ratio map on a pixel by pixel basis between the registered first and second images.

21. A MECT system in accordance with claim 20 wherein said computer further configured to display the ratio map in color as an overlay to a grayscale anatomical image of the lung.

22. A Multi-Energy Computed Tomography (MECT) System comprising:
   a radiation source;
   a radiation detector; and
   a computer operationally coupled to said radiation source and said radiation detector, said computer configured to:
   receive data regarding a first energy spectrum of a scan of a lung of a patient;
   receive data regarding a second energy spectrum of the scan; and
   decompose the received data to generate data regarding a plurality of contrast agents.

23. A computer readable medium encoded with a program configured to instruct a computer to:
   receive data regarding a first energy spectrum of a Computer Tomography (CT) scan of a lung of a patient;
   receive data regarding a second energy spectrum of the CT scan; and
   decompose the received data to generate data regarding a plurality of contrast agents.

24. A computer readable medium encoded with a program configured to instruct a computer to:
   scan a lung of a patient with a Multi-Energy Computed Tomography (MECT) system to acquire data regarding a first contrast agent in a gaseous medium and a second contrast agent in a liquid medium;
   generate a first functional image using data regarding the first contrast agent; and
   generate a second functional image using data regarding the second contrast agent.

25. A method for obtaining data, said method comprising:
   administering a gaseous contrast agent to a patient;
   administering a liquid contrast agent to the patient; and
   imaging the patient to obtain data regarding the gaseous contrast agent and the liquid contrast agent in a single Computer Tomography (CT) data acquisition process.

26. A method in accordance with claim 25 wherein said imaging comprises imaging the patient to substantially simultaneously obtain data regarding the gaseous contrast agent and the liquid contrast agent in a single data acquisition process.

* * * * *